(12) United States Patent
Brugnoli

(10) Patent No.: US 9,999,374 B2
(45) Date of Patent: Jun. 19, 2018

(54) ANTIBACTERIAL FILTER AND TURBINE FLOWMETER FOR TESTS ON RESPIRATORY FUNCTIONALITY

(71) Applicant: COSMED S.R.L., Rome (IT)

(72) Inventor: Paolo Brugnoli, Rome (IT)

(73) Assignee: COSMED S.R.L., Rome (IT)

( * ) Notice: Subject to any disclaimer, the term of this patent is extended or adjusted under 35 U.S.C. 154(b) by 602 days.

(21) Appl. No.: 14/351,966

(22) PCT Filed: Oct. 8, 2012

(86) PCT No.: PCT/IB2012/055427
§ 371 (c)(1),
(2) Date: Apr. 15, 2014

(87) PCT Pub. No.: WO2013/057623
PCT Pub. Date: Apr. 25, 2013

(65) Prior Publication Data
US 2015/0265185 A1 Sep. 24, 2015

(30) Foreign Application Priority Data
Oct. 17, 2011 (EP) ..................................... 11185374

(51) Int. Cl.
*A61B 5/08* (2006.01)
*A61B 5/09* (2006.01)
(Continued)

(52) U.S. Cl.
CPC ................ *A61B 5/09* (2013.01); *A61B 5/097* (2013.01); *B01D 46/0015* (2013.01)

(58) Field of Classification Search
CPC ........ A61B 5/09; A61B 5/097; B01D 46/0015
See application file for complete search history.

(56) References Cited

U.S. PATENT DOCUMENTS 5,003,828 A * 4/1991 van den Burg .......... A61B 5/09
600/539
5,230,727 A * 7/1993 Pound ................ B01D 46/0005
210/446

(Continued)

FOREIGN PATENT DOCUMENTS

CH 627359 A5 1/1982
FR 2560988 A1 9/1985
(Continued)

OTHER PUBLICATIONS

Standardisation of Spirometry; Eur Respir J 2005; 26: 319-338 DOI: 0.1183/09031936.05.00034805 copyrightERS Journals Ltd 2005.
(Continued)

*Primary Examiner* — Tiffany Weston
(74) *Attorney, Agent, or Firm* — Young Basile Hanlon & MacFarlane, P.C.

(57) ABSTRACT

A flowmeter and filter assembly for spirometry have a flowmeter with a turbine rotor and sensor means for detecting the speed of rotation of the rotor, and a filter upstream of the flowmeter. An air-conveying device modifies the direction of the flow of air at an outlet from the filter to set the rotor in rotation within the flowmeter. The air-conveying device is integrated in the filter instead of in the flowmeter.

4 Claims, 8 Drawing Sheets

(51) Int. Cl.
*A61B 5/097* (2006.01)
*B01D 46/00* (2006.01)

(56) References Cited

U.S. PATENT DOCUMENTS

| | | | |
|---|---|---|---|
| 5,337,739 A * | 8/1994 | Lehman | A61B 5/097 128/205.27 |
| 5,390,668 A * | 2/1995 | Lehman | A61B 5/097 128/205.27 |
| 5,419,326 A | 5/1995 | Harnoncourt | |
| 5,997,483 A | 12/1999 | Johnson | |
| 7,618,235 B2 * | 11/2009 | Sacco | A61B 5/09 415/121.3 |
| 2007/0059165 A1 | 3/2007 | Boschetti Sacco | |
| 2008/0249429 A1 * | 10/2008 | Garbe | A61B 5/09 600/539 |
| 2013/0133663 A1 * | 5/2013 | Maksym | A61B 5/097 128/205.27 |

FOREIGN PATENT DOCUMENTS

| | | | | |
|---|---|---|---|---|
| KR | 100930472 | * | 12/2009 | B01D 27/08 |
| KR | 100930472 B1 | | 12/2009 | |
| WO | 2005037102 A1 | | 4/2005 | |
| WO | WO2011/034296 | * | 3/2011 | B01D 27/08 |

OTHER PUBLICATIONS

Lung Volume Equipment and Infection Control; J.L. Clausen; Eur Respir J 1997; 10: 1928-1932.

* cited by examiner

ANTIBACTERIAL FILTER AND TURBINE FLOWMETER FOR TESTS ON RESPIRATORY FUNCTIONALITY

CROSS REFERENCE TO RELATED APPLICATION

The present application claims priority to European Patent Application No. 11185374.3, filed Oct. 17, 2011, incorporated herein in its entirety.

TECHNICAL FIELD

The field of application of the present invention is spirometry, i.e., the evaluation of the respiratory function of a person, for instance in the clinical field (pneumology) or sports field (for example, for the evaluation of the suitability for practising sports activities) or legal field (for example, in the field of occupational medicine).

BACKGROUND

Evaluation tests consist in measuring the flow of air exhaled/inhaled via a flowmeter connected to the mouth of the subject during particular manoeuvres indicated by a skilled operator.

There exist different types of flowmeters. The most common ones are the so-called Fleisch pneumotachograph, Lilly pneumotachograph, Pitot pneumotachograph, mass flowmeter, turbine flowmeter, ultrasound flowmeter and variable-orifice flowmeter.

The present invention regards in particular turbine flowmeters. FIG. 1 of the annexed drawings shows a patient wearing a nose clip A for closing the nostrils in such a way as to convey all the air exhaled into a flowmeter B provided with a grip D. Set between the flowmeter B and the mouth of the patient is an antibacterial filter C, of the disposable type, which is to prevent any contamination in the breathing-in phase. FIGS. 2 and 3 of the annexed drawings show in perspective view and side view, and at an enlarged scale, the antibacterial filter C according to the prior art, comprising a hollow body C1, substantially in the form of a circular disk, with an inlet portion C2 that is to receive a flow of air exhaled by the patient and an outlet portion C3 that is to convey the air that has traversed the filter C towards the flowmeter B. Interposed in the hollow disk-shaped body C1 is a disk of filtering material F (represented with a dashed line in FIG. 3).

FIGS. 4 and 5 are a perspective view and a cross-sectional view and at an enlarged scale of an example of turbine flowmeter according to the prior art.

The flowmeter B comprises a cylindrical tubular body B1, made for example of plastic material, in particular transparent plastic material, defining an inlet portion B2 and an outlet portion B3 for the flow of air that traverses the flowmeter B. Provided within the portions B2, B3 are two conveying devices B4, B5 (FIGS. 4 and 5) comprising a plurality of stationary fins, rigidly connected to the body of the filter B1 and shaped so as to impart a helical direction on the flow of air that traverses it. The structure of the two conveying devices B4, B5 is also used for supporting in a freely rotating way a shaft B6 carrying the blades (for example two blades at 180° or three blades at 120°) of a turbine rotor R. The rotor R, made of plastic material and of low weight, is set in rotation by the flow of air that traverses the flowmeter, after the flow has been converted into in a helical flow by the conveying device B4 at the inlet of the flowmeter.

The speed of rotation of the rotor R is detected by sensor means of any type, for example by means of a pair of photo-emitters Tx1, Tx2 and a pair of corresponding photo-detectors Rx1, Rx2 (see FIG. 6 of the annexed drawings) provided on the body of the flowmeter and designed to detect the interruption of the light beams emitted by the photo-emitters caused by the passage of the blades of the rotor R. The aforesaid optical detection device is consequently able to detect the speed of rotation of the rotor R, as well as also the direction of rotation. The signal at output from the photo-detectors is processed by electronic processing means and thus provides a reliable and accurate indication of the flow and of the volume of air emitted by the patient.

Spirometry is a consolidated technique in medicine. As regards the requirements of the necessary instrumentation, international standardization guidelines are available, amongst which the following may be cited:

ATS/ERS 2005: "STANDARDISATION OF LUNG FUNCTION TESTING" edited by V. Brusasco, R. Crapo and G. Viegi: "Standardisation of spirometry, European Respiratory Journal 2005; 26: 319-338;

ERS/ATS 1997: "*Lung volume equipment and infection control*"; European Respiratory Journal 1997; 10: 1928-1932.

One of the important requirements to be respected in apparatuses for spirometry is the protection of the airways of the patient from contact with viruses and bacteria that may be present in the instrumentation.

Said results can be achieved with the following methods:
1) use of instrumentation in which all the elements in contact with the air exhaled and inhaled by the patient are disposable (disposable flowmeter);
2) interposition of a disposable antibacterial/antiviral filter between the flowmeter and the mouth of the patient;
3) disinfection of all the parts in contact with the air exhaled and inhaled by the patient.

Of the three methods listed above, the last one is not in general considered valid on account of the excessive costs and time involved.

As regards the first two solutions, i.e., use of a disposable flowmeter or adoption of the antibacterial filter, it is important to examine certain aspects in greater depth.

Disposable Flowmeter

The state of the art regarding disposable flowmeters offers different solutions already available on the market (see also the documents Nos. WO 2005/037102 A1, U.S. Pat. No. 5,419,326; U.S. Pat. No. 5,997,483). The main difficulties that are encountered in producing an entirely disposable flowmeter are the following:
  it is difficult to keep the production cost low;
  if the disposable flowmeter includes components that can alter the response of the flowmeter, it is necessary to calibrate the spirometer after each replacement of the flowmeter or to codify the flowmeter on the basis of the response given;
  no other part of the spirometer must come into contact with the air exhaled/inhaled by the subject in so far as no protective barrier constituted by an antibacterial filter is present.

Disposable Antibacterial Filter

The use of a disposable antibacterial filter (for example, of the type illustrated in FIGS. 1-3 of the annexed drawings)

is recommended by all standardization guidelines, where it is also necessary for the following requirements to be respected:

the expiratory resistance of the ensemble flowmeter plus filter must not exceed the limit of 1.5 cm $H_2O$/l/s, up to flows of 14 l/s so as to guarantee that the results are not altered;

the connection between the filter and the flowmeter must be completely fluid-tight so that all the air exhaled by the patient is effectively measured;

the efficiency of the filtering barrier against the passage of viruses and bacteria must be adequate and demonstrated with tests conducted by independent bodies.

Further considerations should moreover be added that do not commonly appear in the technical literature in this field, but that are equally important for the reliability of the measurements and the safety of the patient.

The response of any flowmeter can vary significantly according to the form of the antibacterial filter connected thereto (the geometry of the filter affects the characteristics of the air flow, with generation of possible turbulence).

There are available on the market low-cost and poor-quality disposable antibacterial filters, which have reduced filtering power and do not ensure the necessary performance.

At times it happens that an antibacterial filter is connected to a flowmeter having a diameter incompatible using adapter connectors that frequently introduce undesirable losses and increase the deadspace of the measuring system (i.e., the volume of air that the patient is forced to breathe again) in an unacceptable way and to the point of altering the fluid-dynamic characteristics for which the device is designed.

SUMMARY

The object of the present invention is to overcome the drawbacks discussed above.

With a view to achieving the aforesaid purpose, the subject of the invention is a flowmeter and filter assembly, comprising:

a flowmeter including a body defining a passage for a flow of air and having an inlet portion and an outlet portion, and a rotor, which is rotatably mounted within said flowmeter body and can be set in rotation by a flow of air that traverses the flowmeter;

a filter, preferably a disposable one, including a body defining a passage for a flow of air and having an inlet portion and an outlet portion which can be connected to the inlet portion of the body of the flowmeter;

an air-conveying device set upstream of the rotor of the flowmeter and configured for modifying the direction of the flow of air directed towards the rotor in such a way as to set said rotor in rotation; and sensor means associated to the aforesaid flowmeter, for detecting the speed of rotation of the rotor;

said flowmeter assembly being characterized in that the air-conveying device set upstream of the rotor forms part of the aforesaid filter and not of said flowmeter.

Thanks to the characteristics indicated above, the flowmeter and filter assembly according to the invention enables all the drawbacks of the known art that have been above discussed above to be overcome. In particular, integration in the filter of the air-conveying device that is set upstream of the rotor renders imperative the production of filters that use materials and constructional techniques with good standards of quality such as to guarantee the desired performance without altering in an unforeseeable way the response of the flowmeter and without introducing undesirable fluid-dynamic losses. In particular, thanks to the aforesaid characteristics, the expiratory resistance of the flowmeter and filter assembly guarantees in all cases the respect of the limits envisaged by the international recommendations (ATS/ERS). Since the filter integrates the aforesaid air-conveying device, the filter itself must be provided for being uniquely designed for the respective flowmeter (which is without conveyor of air upstream of the rotor), which rules out the possibility of using an inadequate connection between the filter and the flowmeter and thus prevents the risk of inadequate measurements and/or of contamination for the patient.

The subject of the invention is also the filter taken in itself, preferably of a disposable type, which can be coupled on the inlet mouth of a flowmeter for spirometry, said filter comprising a body defining a passage for a flow of air and having an inlet portion and an outlet portion and a filtering means interposed within said passage, and being moreover characterized in that it incorporates an air-conveying device configured for modifying the direction of the flow of air at outlet from the filter.

Finally, the subject of the invention is also the flowmeter taken in itself, which is designed to co-operate with the filter of the invention and consequently without an air-conveying device upstream of the rotor.

BRIEF DESCRIPTION OF DRAWINGS

Further characteristics and advantages of the invention will emerge from the ensuing description with reference to the annexed drawings, which are provided purely by way of non-limiting example and in which.

DESCRIPTION OF EMBODIMENTS

In FIGS. 7-11, the parts in common with the ones illustrated in FIGS. 1-6 are designated by the same reference numbers.

Figure 1:
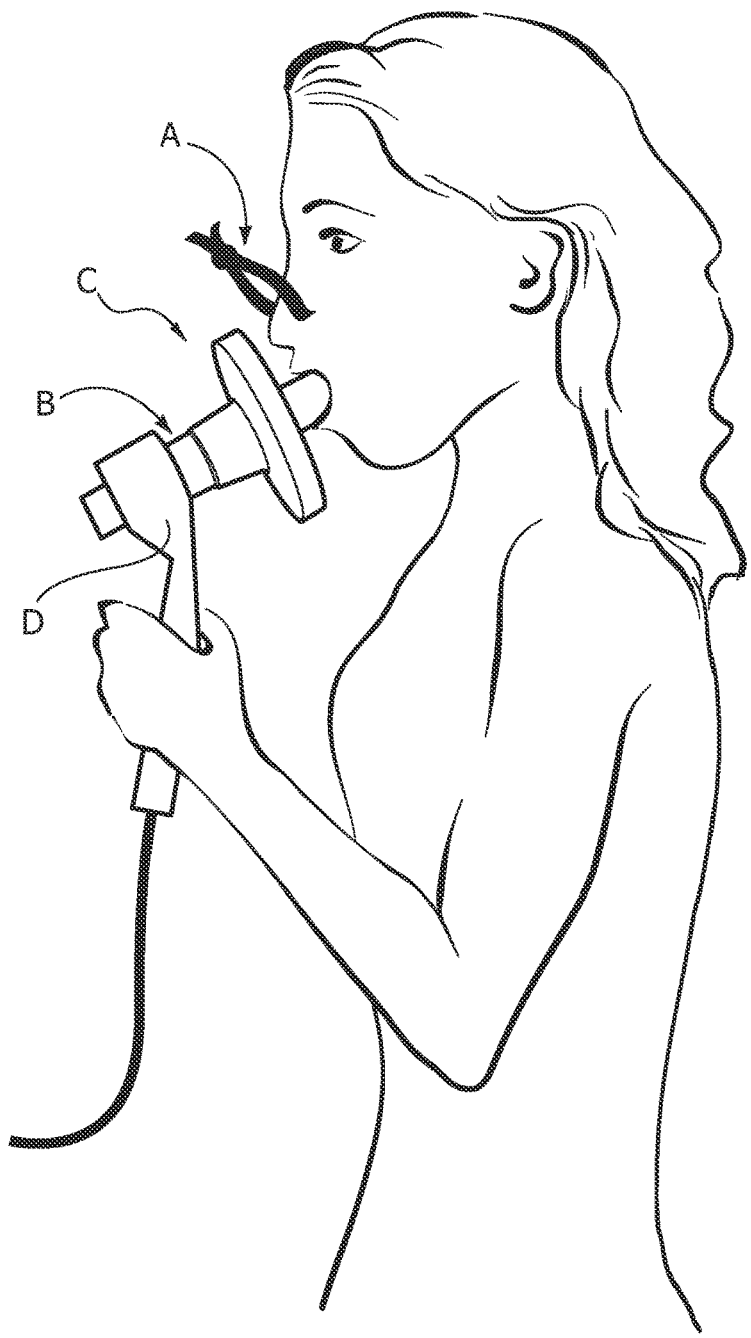
FIG. 1, already described above, shows the use of a flowmeter provided with an antibacterial filter of the turbine type.
Figure 2:
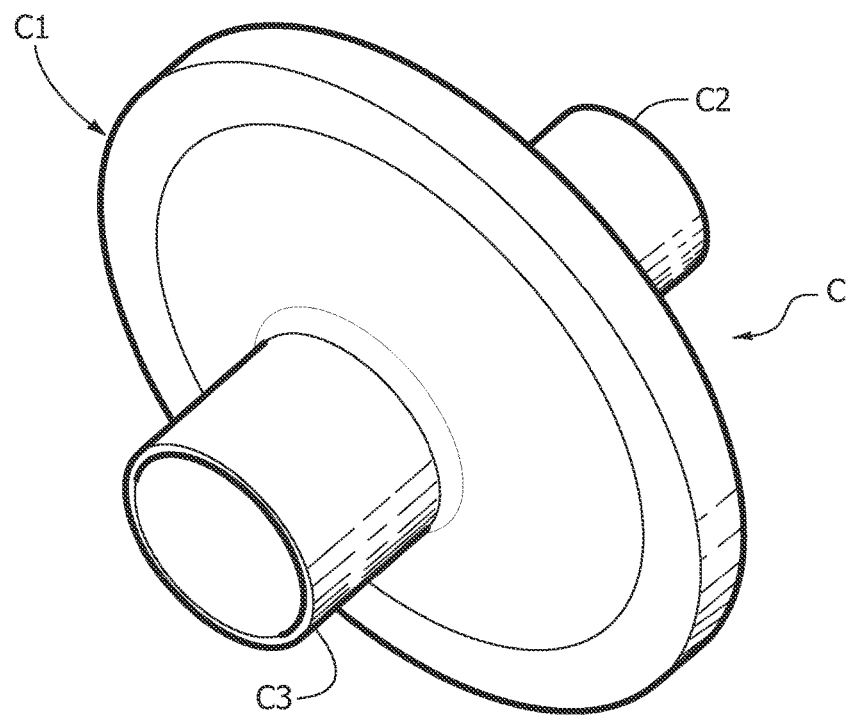
FIGS. 2 and 3 are a perspective view and a side view, respectively, of an antibacterial filter according to the prior art.
Figure 3:
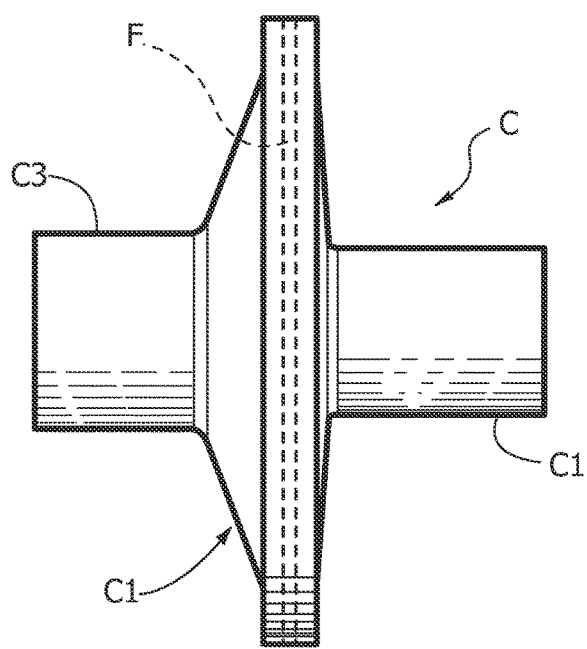
Figure 4:
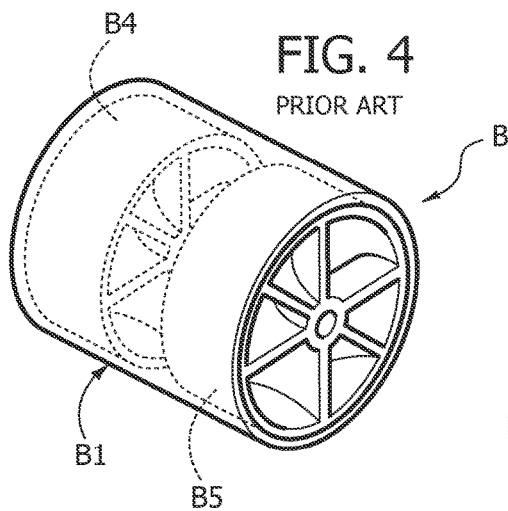
FIG. 4 and FIG. 5 are, respectively, a perspective view and a cross-sectional view and at an enlarged scale of a turbine flowmeter according to the prior art.
Figure 5:
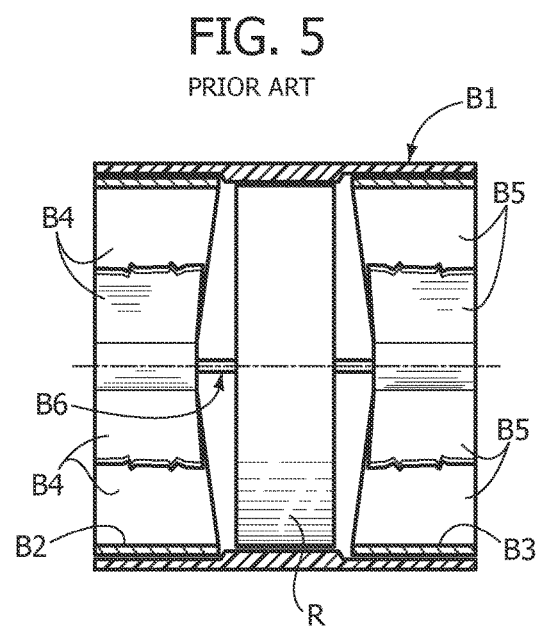
Figure 6:
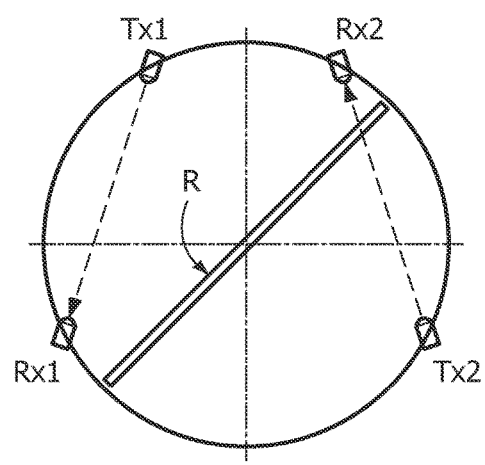
FIG. 6 is a schematic cross-sectional view in a plane orthogonal to the axis of the filter that shows the working principle of the sensors of the speed of rotation of the rotor of the flowmeter, provided according to the prior art.
Figure 7:
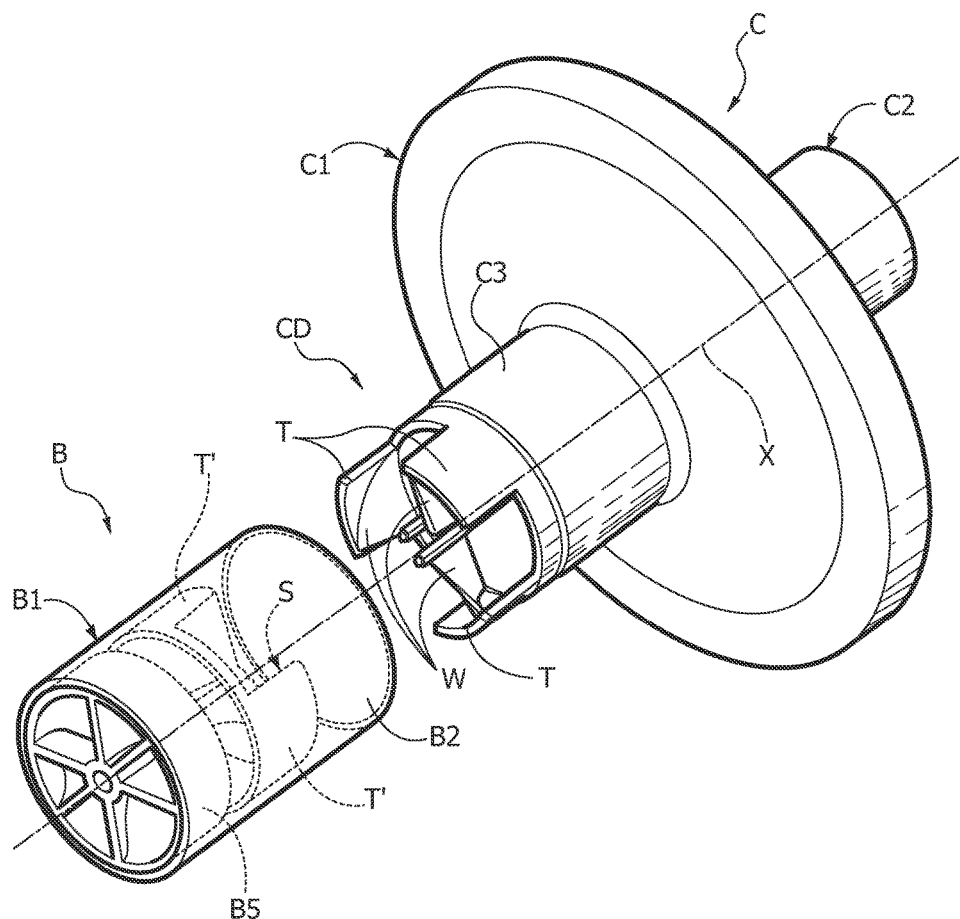
FIGS. 7 and 8 are exploded perspective views of a preferred embodiment of the flowmeter and filter assembly according to the present invention.
Figure 8:
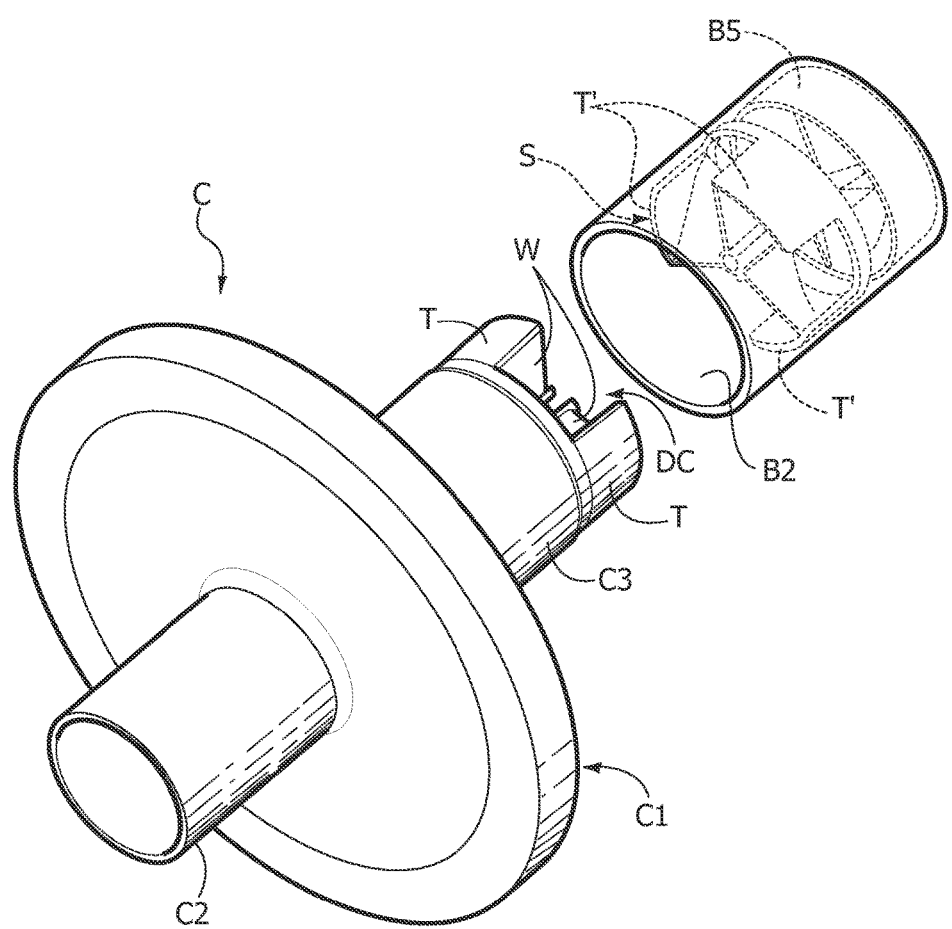

FIG. 1 of the annexed drawings, which shows the use of the flowmeter by a patient, also applies to the case of the assembly according to the invention. Also in this case, the assembly comprises a flowmeter B, which can be accommodated within a grip D and is provided with an antibacterial filter C for use by the patient.

With reference to FIGS. 7-11, also in the case of the preferred embodiment of the invention that is illustrated here, the filter C has a hollow body C1, for example made of plastic material, substantially in the form of a circular disk, with a tubular inlet portion C2 and a tubular outlet portion C3 projecting from the opposite faces of the disk body C1 and set coaxially with respect to the latter.

It should be noted that the general conformation of the antibacterial filter C can also be altogether different from the one illustrated herein purely by way of example, the only essential condition, for the purposes of the invention, being that the outlet portion C3 of the antibacterial filter incorporates an air-conveying device DC configured for modifying the direction of flow of air at outlet from the filter C.

In the case of the example illustrated, the conveying device DC comprises three stationary fins W rigidly connected to the body C1 of the filter. The fins W are set at equal angular distances apart about the axis X of the filter C and are shaped for imparting a helical direction on the flow of air at outlet from the filter, such as to set the rotor R of the flowmeter in rotation. The fins W extend in the direction of the axis X starting from respective axial tabs T that project from the end front edge of the tubular outlet portion C3 of the filter C.

Figure 9:
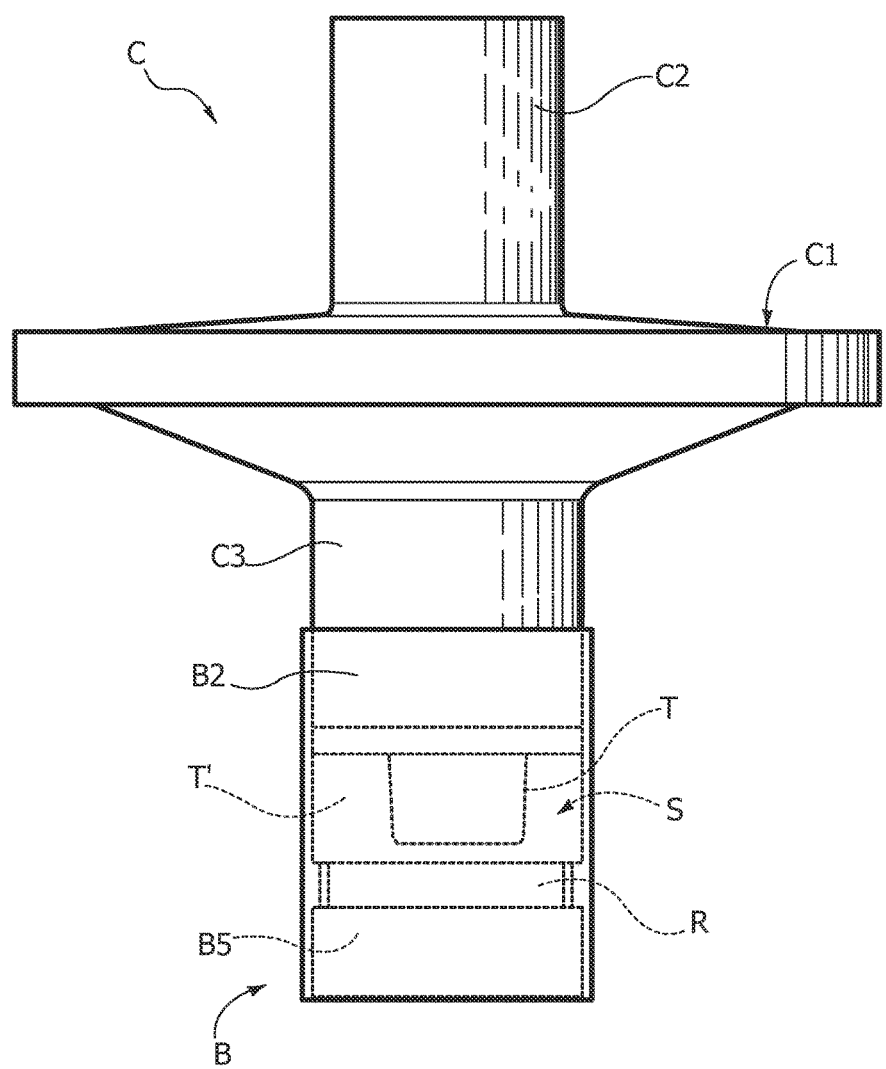
FIG. 9 is a side view of the assembly according to the invention in the assembled condition.
Figure 10:
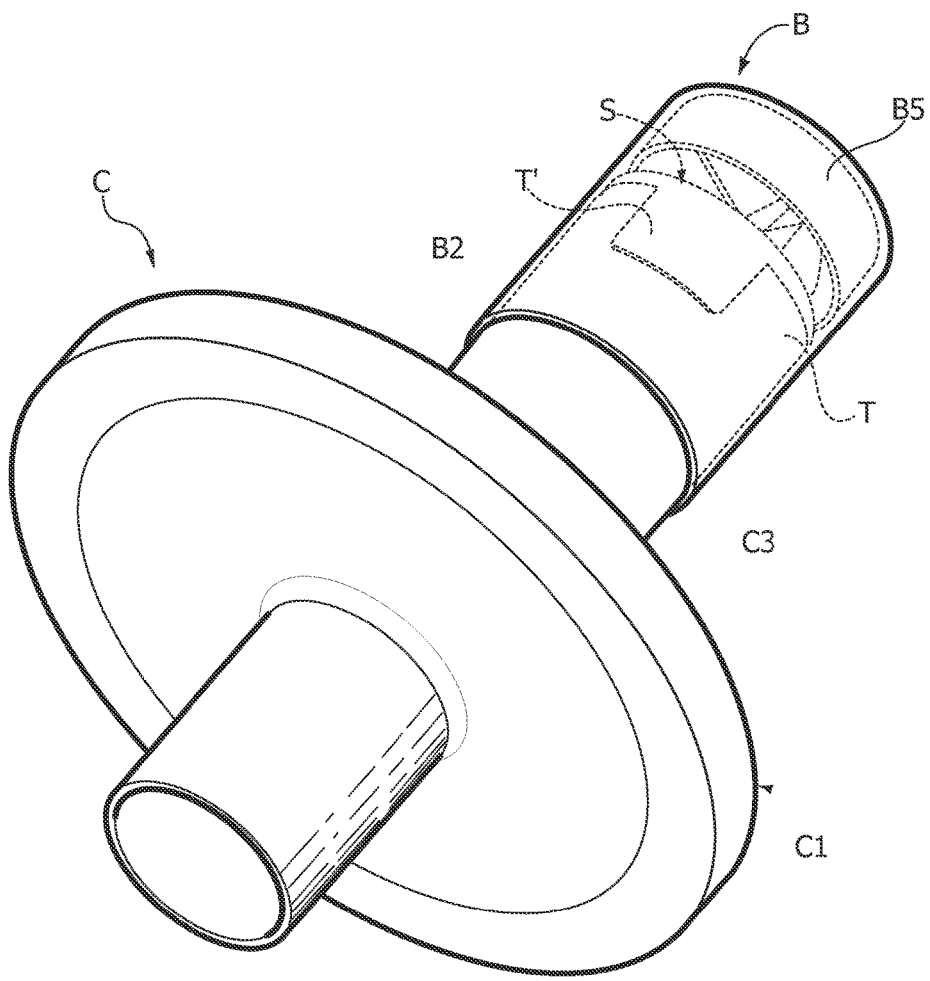
FIGS. 10 and 11 are two further perspective views of the preferred embodiment of the flowmeter and filter assembly according to the invention.
Figure 11:
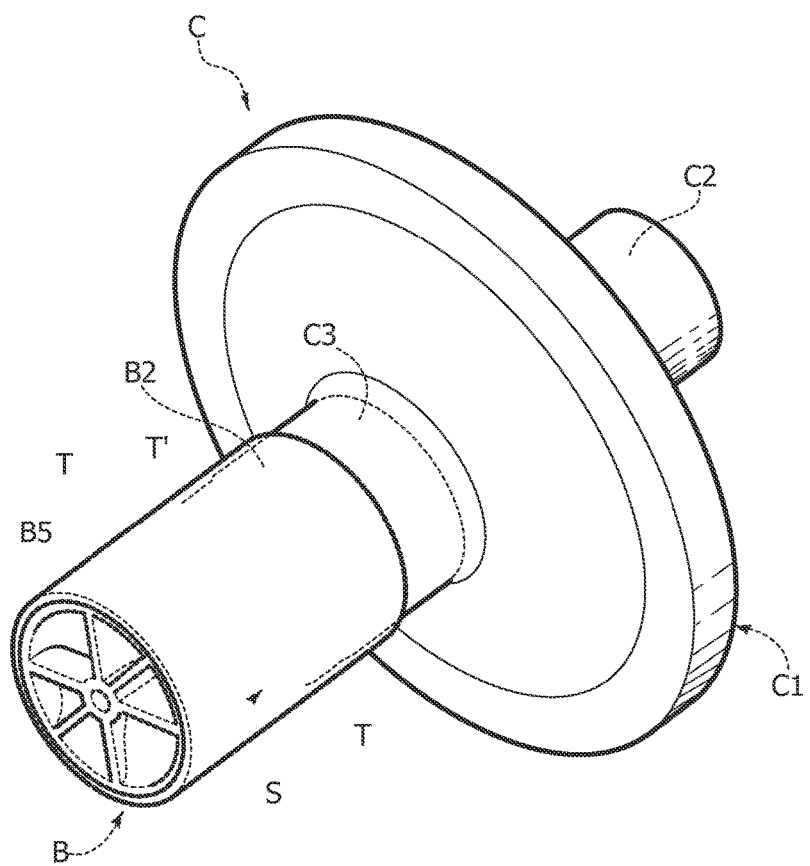

With reference once again to FIGS. 7-11, the flowmeter B according to the invention comprises, in the embodiment illustrated, a cylindrical body B1, for example made of plastic material, and in particular of transparent plastic material, having a tubular conformation. The body B1 has an end portion, which is fitted with slight interference on the tubular outlet portion C3 of the filter (FIG. 9). Within the body B1 of the flowmeter, a rotor R is rotatably mounted about the axis X of the flowmeter (see FIG. 9). The rotor is carried by a shaft that is mounted so that it can rotate freely within the body B1 of the flowmeter B. For this purpose, one end of the shaft of the rotor is rotatably supported by the hub of an air-conveying device B5 similar to that of the conventional flowmeter that has been described in greater detail above and is mounted within the outlet end of the flowmeter B, i.e., downstream of the rotor. Upstream of the rotor, the flowmeter B is without any air-conveying device, the corresponding end of the shaft of the rotor being supported in rotation by a supporting body S inserted within the flowmeter B, which does not have any function of conveying the flow of air; i.e., it is not able to modify to any great extent the direction of the flow of air. The support S comprises three peripheral tabs T' that are inserted into the respective compartments comprised between the tabs T of the filter in the condition where the flowmeter is coupled to the filter, in which the cylindrical wall of the body B1 of the flowmeter is set on the outside of the cylindrical outlet portion C3 of the filter, and the tabs T' of the flowmeter are inserted between the tabs T projecting from the front edge of the tubular outlet portion C3 of the filter.

Hence, as emerges clearly from the drawings, the disposable filter C is made for being uniquely coupled to the flowmeter B that has been described previously.

As already mentioned, the only essential characteristic for the purposes of the present invention lies in the fact that the air-conveying device set upstream of the rotor of the flowmeter is integrated in the outlet portion of the filter instead of being provided in the flowmeter. Of course, without prejudice to said essential characteristic, the details of construction and the embodiments both of the filter and of the flowmeter, as well as of the parts for coupling between the flowmeter and the filter, can vary widely with respect to what has been described herein purely by way of example.

Furthermore, even though the invention has been devised particularly for use of a disposable filter, it is not ruled out that it may be used also for a non-disposable filter.

As is evident from the foregoing description, the invention opens the way to a new generation of filters, which are characterized not only in that they perform a filtering function but also in that they integrate an air-conveying device that is able to modify the direction of the flow of air at outlet from the filter in order to set the rotor of the flowmeter connected to the filter in rotation. Said solution renders production of filters with materials and constructional techniques of good quality compulsory also in the case of filters of a disposable type, a fact that guarantees an optimal performance and a high reliability as regards the measurements made and in terms of safety for the patient.

The invention claimed is:

1. A disposable filter for spirometry for use in connection to a separate and independent flowmeter for spirometry, the filter comprising:
    a filter hollow body having a longitudinal axis and defining a passage for a flow of air through the filter hollow body, the filter hollow body further comprising:
        a filter inlet portion;
        a filter circular disk portion in fluid communication with and positioned downstream of the inlet portion, the circular disk portion having a peripheral edge radially larger than the inlet portion about the longitudinal axis;
        a filtering material positioned in the circular disk portion; and
        a filter tubular outlet portion in fluid communication with and positioned downstream of the circular disk portion, the tubular outlet portion further comprising:
            a plurality of filter axial tabs extending longitudinally along the longitudinal axis and having a filter outlet end, the plurality of filter axial tabs operable to engage a body of the separate and independent flowmeter; and
            a filter air-conveying device comprising:
                a plurality of stationary filter fins rigidly connected to the filter tubular outlet portion, each filter fin connected to a respective filter axial tab and radially and helically extending inward inside the filter hollow body toward and about the longitudinal axis in the flow of air passage, the plurality of stationary fins operable to modify the direction of the flow of air in the passage inside the filter hollow body to a helical direction at the filter hollow body outlet end.

2. The filter according to claim 1 wherein each axial fin further comprises a distal end extended into the filter flow of air passage, the distal end free from connection to other of the plurality of axial fins.

3. The filter according to claim 1 wherein the plurality of filter fins are equally angularly spaced apart from one another about the filter tubular outlet portion.

4. The filter according to claim 1, wherein the filter outlet portion is configured for coupling with a complementary portion defined on an inlet portion of the flowmeter.

* * * * *